United States Patent [19]

Boonstra

[11] 4,068,168

[45] Jan. 10, 1978

[54] ELECTRICAL RESISTIVITY PROBE MEANS

[76] Inventor: Bram Bernard Boonstra, 145 Maskwonicut St., Sharon, Mass. 02067

[21] Appl. No.: 729,256

[22] Filed: Oct. 4, 1976

[51] Int. Cl.² ............................................. G01R 27/02
[52] U.S. Cl. .................................................. 324/65 R
[58] Field of Search ....................... 324/65 P, 65 R, 64

[56] References Cited

U.S. PATENT DOCUMENTS

| | | | |
|---|---|---|---|
| 1,610,563 | 12/1926 | McIlvaine | 324/65 R |
| 2,142,619 | 1/1939 | Sciaky | 324/64 |
| 2,437,697 | 3/1948 | Kalom | 324/65 R X |
| 2,532,929 | 12/1950 | McBrayer | 324/65 R |
| 2,621,232 | 12/1952 | Spalding | 324/65 P |
| 2,993,168 | 7/1961 | Burnette, Jr. | 324/65 R X |
| 3,141,129 | 7/1964 | Dietert | 324/65 P |
| 3,229,200 | 1/1966 | Rayburn | 324/65 R X |

FOREIGN PATENT DOCUMENTS 517,212  2/1931  Germany ........................... 324/65 P Primary Examiner—Stanley T. Krawczewicz

[57] ABSTRACT

There is disclosed an electrical resistivity probe means adapted to cut and receive a sample of compliant test material therein. The probe means of the invention is useful, for instance, for the measurement of electrical resistivity of compliant materials having dispersed therein one or more electrically conductive fillers.

10 Claims, 5 Drawing Figures

ELECTRICAL RESISTIVITY PROBE MEANS

BACKGROUND OF THE INVENTION

The present invention relates to means for determining the electrical resistivity characteristics of compliant materials such as unvulcanized rubber-carbon black compounds.

It is well known that the resistivity of a vulcanized rubber-carbon black compound is dependent on the degree of mixing of the black and rubber in the mixing machine during preparation of the unvulcanized compound. During compounding of the unvulcanized rubber compound, the electrical resistivity of the compound tends to reach a minimum value when the black is just incorporated and in its minimum state of dispersion in the matrix. At this stage the carbon black forms a random, loose, and not completely coherent network. Past this point of minimum dispersion, however, the carbon black network is broken up into smaller domains which are more distantly spaced as more shear and mixing energy is dissipated into the compound. As a consequence of this destruction and dispersion of the carbon black network, the electrical resistivity of the compound increases. Therefore, electrical resistivity is a property which reflects the degree of dispersion of the carbon black (or other electrically conductive filler) and it is understandable that attempts should be made to use electrical resistivity measurement of a compliant material containing an electrically conductive filler as a means of monitoring the quality of dispersion of said filler. Where carbon black is concerned, high quality dispersions thereof in rubbers are generally desirable in order to assure development of optimum physical properties in the final vulcanizates. However, the time involved in the preparation of vulcanized form-stable samples mitigates against use of an electrical resistance test method as a rapid way of assessing the degree of dispersion of an electrically conductive filler in a rubber compound.

It can be assumed that a similar relationship as between degree of dispersion of an electrically conductive filler and resistivity of the ultimate vulcanizates also exists in the unvulcanized compound, in other words, prior to curing thereof. Here, however, the difficulties encountered in measuring unvulcanized compound resistivity are extensive and, insofar as is known to the present applicant, the literature does not mention systematic measurement of unvulcanized compound resistivity as a variable test for the quality of filler dispersion. The difficulties attendant resistivity testing of unvulcanized rubber compounds are outlined below.

Firstly, the instrument probe electrodes must make good contact with the compound under test and this implies that the electrodes must, of necessity, be forced onto the compound under high pressure. On the other hand, application of electrodes under high pressure to an unvulcanized rubber compound sample causes flow and distortion of the sample, thus interfering with the dimensional stability of the sample and upsetting the equilibrium state of the filler dispersion therein. This phenomenon results in erratic electrical resistivity test values. Heretofore, in order to give an unvulcanized rubber sample sufficiently stable and defined dimensions as to ameliorate the problem, it has generally been necessary to form the sample by pressing it for some time in a mold and at a somewhat elevated temperature. This expedient, however, also defeats the achievement of the goal of rapid measurement of unvulcanized compound resistivity. In accordance with the present invention, this problem has been resolved.

As used herein, the term "resistivity" refers to the apparent resistivity of a compound. Said apparent resistivity may also include a contribution from the contact resistance between electrodes and compound.

OBJECTS OF THE INVENTION

The principal object of the invention is to provide a novel probe means for the rapid measurement of the electrical resistivity of compliant materials containing an electrically conductive filler dispersed therein.

It is another object of this invention to provide probe means for measuring the quality of dispersion of a carbon black filler contained in an unvulcanized rubber matrix as a function of apparent electrical resistivity.

It is another object of the invention to provide electrical resistivity probe means by which the contribution of contact resistance of the probe electrodes with a sample under test is minimized.

It is another object to provide electrical resistivity probe means adapted to rapidly fabricate compliant material samples of uniform dimensions.

It is another object of the invention to provide electrical resistivity probe means which fabricates compliant material samples and retains them in dimensionally stable condition.

It is still another object of the invention to provide electrical resistivity probe means that is simple and easy to maintain and easy to clean.

It is still another object of the invention to provide electrical resistivity probe means adapted to receive a compliant material sample therein and adapted to rapidly eject said sample therefrom.

Other objects and advantages of the present invention will in part be obvious and will in part appear hereinafter.

SUMMARY OF THE INVENTION

The electrical resistivity probe means of the invention broadly comprises, in combination: a tubular member having a rim adapted to cut into a compliant test material, said tubular member comprising a first electrode; a solid electrically insulative roof member bridging the bore of said tubular member and being upwardly displaced from the rim thereof, thereby to define a sample receiving chamber thereunder; a second electrode spaced from said first electrode; a solid electrically insulative floor member adapted to support a sample of compliant material thereon, said floor member being fixedly spaced under the rim of said tubular member and means to traverse the rim of said tubular member downwardly through a compliant material sample stationed on said floor member.

THE DRAWINGS

Figure 1:
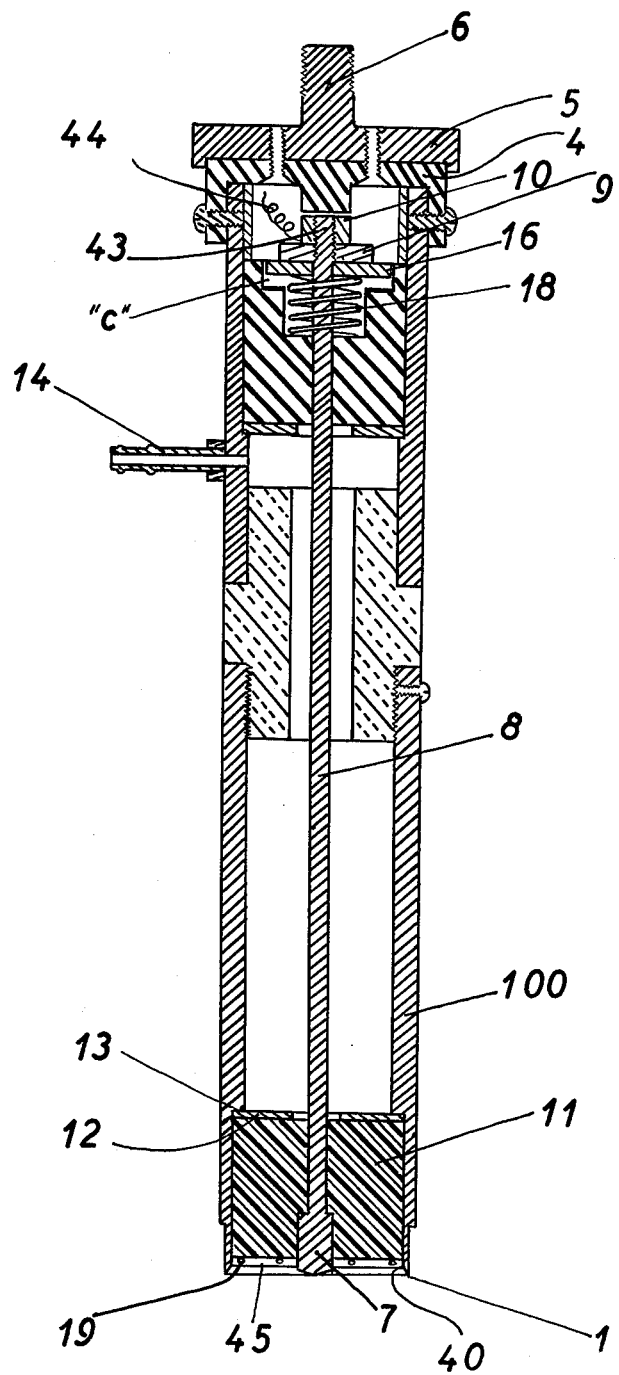
FIG. 1 is a diagrammatic partly sectional side view of the resistivity probe means of the invention.
Figure 2:
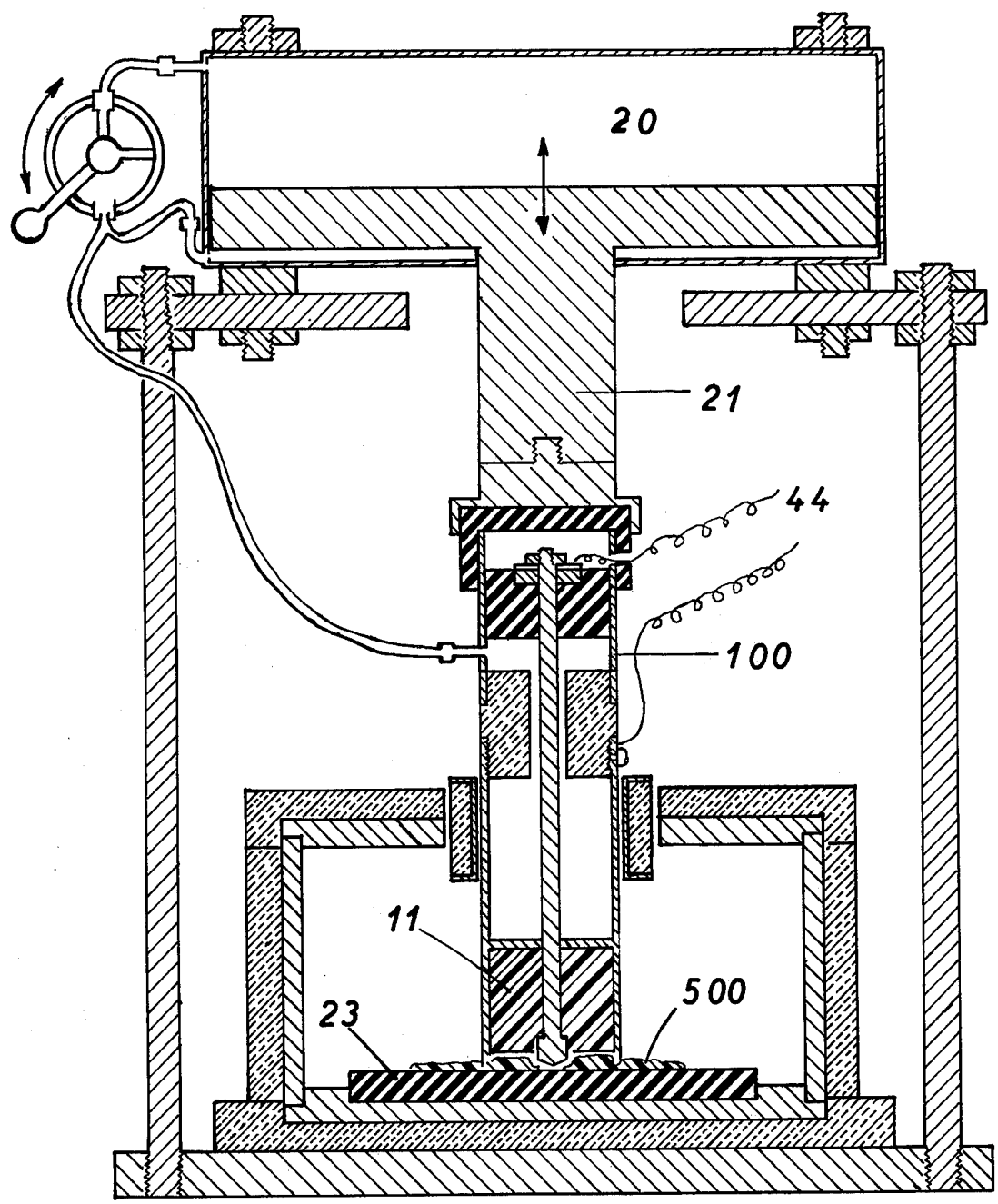
FIG. 2 is a diagrammatic partly sectional side view showing a suitable electrical resistivity test arrangement embodying the probe means of FIG. 1 and the floor means of FIGS. 3 and 4.
Figure 3:
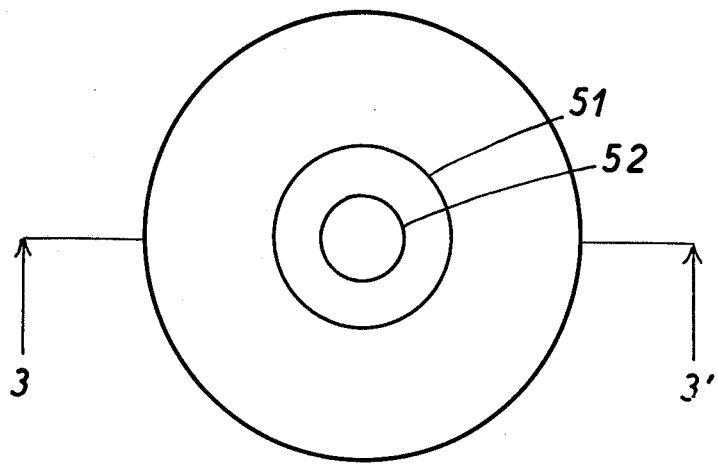
FIG. 3 is a diagrammatic top view of electrically insulative floor means suitable for use with the probe means of the invention.
Figure 4:
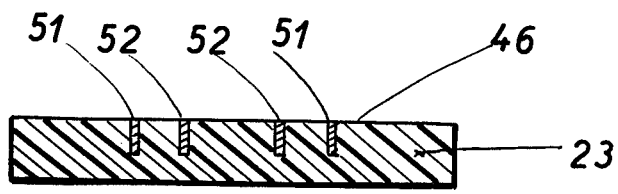
FIG. 4 is a diagrammatic sectional side view of the insulative floor means of FIG. 3, taken through line 3-3' thereof.

Referring now to FIGS. 1 through 3, wherein like reference numerals refer to like structures, there is shown a tubular member 100 having a rim 1 adapted to cut into a compliant test material 500 stationed thereunder. Said tubular member 100 also comprises a first electrode 40 adapted to place said tubular member into electrical communication with a cut sample of the compliant test material 500. In the specific embodiment shown in the drawing, said first electrode 40 constitutes the entire circumference of said tubular member 100 and, while this is a preferred embodiment of the tubular member 100 of the invention, said first electrode 40 need not constitute the entire circumference of the tubular member 100.

A solid electrically insulating roof member 11 bridges the bore of said tubular member 100 and is displaced upwardly from the rim thereof, thereby to define thereunder a sample receiving chamber 45. Desirably, said roof member 11 is slidably engaged in the bore of said tubular member and is provided with means to temporarily traverse it downwardly relative to rim 1, thereby to eject a compliant material sample contained in said sample receiving chamber 45. One such traverse means is shown in the drawing and will be explained in more detail hereinafter.

A second electrode 7 is provided in spaced relationship with respect to first electrode 40. As shown in the embodiment specifically depicted in FIGS. 1 and 2, said second electrode 7 is attached to a metal rod 8 which runs the length of the bore of tubular member 100 and terminates with a threaded end 43 having a nut 9 and counternut 10, between which a suitable electrical lead 44 may be attached. As will be noted, the shaft 8 runs through insulative roof member 11. The insulative roof member 11 is supported by a ring 12 held in an internal shoulder 13 cut into the bore of tubular member 100. A working fluid inlet 14 communicates with that portion of the bore of the tubular member 100 residing above the insulative roof member 11 and is connected to a suitable working fluid source such as source of compressed air. Upon completion of a resistivity measurement, the compressed fluid is introduced through inlet 14, thereby to cause downward movement of second electrode 7 along with electrically insulative roof member 11 relative to the rim 1 of tubular member 100, thereby to eject a compliant material sample from residence in the sample receiving chamber 45. This downward movement of the second electrode 7 and roof member 11 is restricted by the range of movement available to the washer 16 which is connected to shaft 8 and which range of movement can be preselected and adjusted by adjustment of nuts 9 and 10 on the threaded end 43 of shaft 8. Return of the second electrode 7 and roof member 11 to their measuring position and the reconstitution of the sample measuring chamber 45 is accomplished by exhausting the working fluid from the bore of tubular member 100, thereby to allow compression spring 18 to act in retrograde fashion against washer 16, shaft 8 and roof member 11.

A stiff electrically insulative floor member 23, which may be composed of polytetrafluoroethylene, for instance, is fixedly spaced under the rim 1 of tubular member 100, the principal purpose of said floor member 23 being to act as a firm support for the compliant material 500 undergoing test.

Completing the probe arrangement of the invention, there is provided means to traverse the rim 1 of tubular member 100 downwardly through a sample of compliant material residing on the surface 46 of floor member 23. In the particular embodiment of the invention depicted in the drawing, said traverse means is a compressed fluid actuator comprising a cylinder 20/piston 21 arrangement. The cylinder 20 is held in fixed position, relative to the floor member 23, while the piston 21 is affixed to the threaded end 6 of cap 5 which, in turn is affixed through insulator 4 to the tubular member 100. It will be appreciated, of course, that this traverse means can be provided by many mechanical or electromechanical arrangements other than the specific compressed fluid actuator arrangement shown. For instance, a solenoid or a manually operated traversing arrangement such as a toggle lever arrangement can also be employed as the rim 1 traversing means.

In the accomplishment of a resistivity measurement, referring now specifically to FIGS. 1 and 2, a compliant material sample 500 is placed on the surface of insulative floor member 23 and the rim 1 of tubular member 100 is traversed downwardly by the action of a working fluid being admitted into cylinder 20, thereby to actuate piston 21. The rim 1 which is preferably internally beveled to a sharp edge, is thusly forced through the compliant material sample 500, thereby cutting therefrom a sample of well-defined dimension and which sample is forced upwardly into the sample receiving chamber 45 wherein said sample is maintained in a dimensionally stable condition during the resistivity testing thereof. In the case of unvulcanized rubber compliant test materials, the force required to cut clean samples during the downward traverse of the rim 1 can generally be from about 25 to about 250 kg or even more. Preferably, the downward force applied to the rim 1 will be on the order of between 100 to about 200 kg. During reception of the cut sample into sample receiving chamber 45 any entrapped air above said sample may be conveniently relieved by one or more of small relief apertures 19 located flush with the bottom of the insulative roof member 11.

Once having thus been fabricated and received into the sample receiving chamber 45, the apparent resistivity of the compliant material test sample may be conveniently determined by placing the first electrode 40 and second electrode 7 in circuit with an electrometer or ohmmeter (not shown). In a preferred embodiment of the probe means of the invention, however, the contribution of contact resistance to the overall apparent resistivity of the sample under test can be substantially suppressed. Where this preferred embodiment of the invention is desired to be utilized, the first electrode 40 and second electrode 7 are placed in circuit with a source of electricity and are employed solely to apply a known current to the compliant material sample residing in sample receiving chamber 45. Also, in this preferred embodiment of the invention, the fixed insulative floor member 23 is provided with a pair of spaced-apart third and fourth electrodes 51 and 52, respectively, which are embedded into and flush with the upper surface thereof. Said spaced apart third and fourth electrodes 51 and 52 are located at fixed positions intermediate the first electrode 40 and second electrode 7 and are preferably arranged in such a manner as to provide essentially line contact with the bottom of the compliant material test sample receiving chamber 45. To this end said third and fourth electrodes 51 and 52 can each be conveniently composed of a metallic foil or shimstock embedded edgewise into the upper surface of the insulative floor member 23. Employing this arrangement, a known current is applied to the sample under test through first and second electrodes 40 and 7 and the third and fourth electrodes 51 and 52 are placed in circuit with a high impedance electrometer, thereby to determine the voltage drop thereacross without contribution thereto by contact resistance of the electrodes 40 and 7.

It is preferred, though not necessary, that the electrode 40 associated with the tubular member 100 be of circular geometry. Where this condition is met, it is further preferred that the second electrode 7 be coaxial with respect to first electrode 40 and that third and fourth electrodes 51 and 52, if employed, also be of circular geometry and coaxially positioned with respect to said circular first electrode 40.

Obviously, many changes and modifications may be made in the above description and drawings without departing from the essential spirit and scope of the invention. For instance, the geometries of the respective electrodes need not be circular but can be adapted to specific needs.

Figure 5:
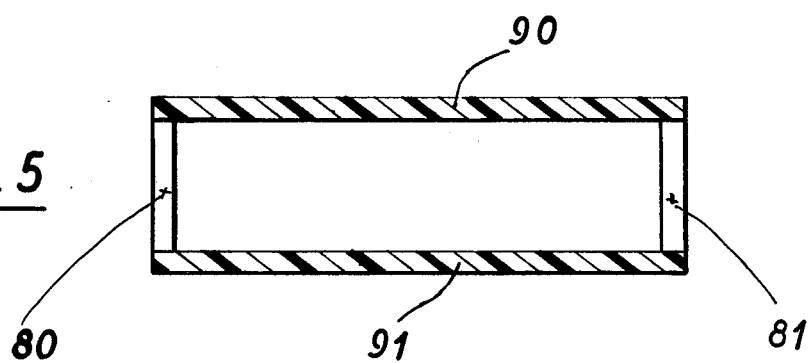
FIG. 5 is a diagrammatic sectional top view of an alternate embodiment of the tubular member element of the invention.

A suitable example of such a variation in electrode geometry is depicted in FIG. 5 wherein there is shown a rim element 1 of rectangular shape. In this instance, a first electrode 80 comprises one of the short sides of the rectangular structure while the second electrode 81 comprises the other short side and is spaced from said first electrode 80 by electrically insulative parallel spaced-apart relatively longer members 90 and 91 of the rectangular rim 1 structure.

Accordingly, the above description is intended to be illustrative in nature and is in no way limiting of the invention.

The embodiments of the invention in which an exclusive property or privilege is claimed are defined as follows:

1. An electrical resistivity probe means comprising, in combination:
   a tubular member having a rim adapted to cut into a compliant test material, said tubular member comprising a first electrode;
   a solid electrically insulative roof member bridging the bore of said tubular member and being displaced upwardly from the rim thereof, thereby to define a sample receiving chamber thereunder;
   a second electrode spaced from said first electrode;
   a solid electrically insulative floor member fixedly spaced under the rim of said tubular member and being adapted to support a sample of compliant test material thereon; and
   means to traverse the rim of said tubular member downwardly through a compliant test material stationed on said floor member.

2. The probe means of claim 1 wherein said first electrode comprises the entire circumference of said tubular member.

3. The probe means of claim 1 wherein said means to traverse the rim of said tubular member comprises a compressed fluid actuator having a fixed member relative to said insulative floor member and a traversing member affixed to said tubular member.

4. The probe means of claim 3 wherein said fixed member is a cylinder and said traversing member is a piston.

5. The probe means of claim 1 wherein said first electrode is circular.

6. The probe means of claim 5 wherein said second electrode is coaxially located with respect to said first circular electrode.

7. The probe means of claim 1 wherein, in addition to said first and second electrodes, said insulative floor member comprises third and fourth spaced apart electrodes flush with the upper surface thereof, which third and fourth electrodes are located at fixed positions intermediate said first and second electrodes.

8. The probe means of claim 7 wherein said third and fourth electrodes are adapted to provide line contact thereof with a compliant test material stationed on said floor member.

9. The probe means of claim 7 wherein said first, third and fourth electrodes are circular and said second, third and fourth electrodes are coaxially located with respect to said first electrode.

10. The probe means of claim 1 wherein said insulative roof member is slidably engaged within the bore of said tubular member and is provided with means to temporarily traverse it downwardly with respect to the rim of said tubular member, thereby to eject a compliant material sample contained in said sample receiving chamber.

* * * * *